US011186535B2

(12) United States Patent
Kim et al.

(10) Patent No.: US 11,186,535 B2
(45) Date of Patent: Nov. 30, 2021

(54) METHOD FOR PRODUCING ALKYL LACTATE

(71) Applicant: CJ CHEILJEDANG CORPORATION, Seoul (KR)

(72) Inventors: Jieun Kim, Gunpo-si (KR); Changyub Oh, Yongin-si (KR); Chang Suk Lee, Yongin-si (KR); Young Lyeol Yang, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 119 days.

(21) Appl. No.: 16/492,852

(22) PCT Filed: Jan. 10, 2018

(86) PCT No.: PCT/KR2018/000455
§ 371 (c)(1),
(2) Date: Sep. 10, 2019

(87) PCT Pub. No.: WO2018/169181
PCT Pub. Date: Sep. 20, 2018

(65) Prior Publication Data
US 2021/0139406 A1     May 13, 2021

(30) Foreign Application Priority Data

Mar. 15, 2017 (KR) .................. 10-2017-0032537
Jul. 25, 2017 (KR) .................. 10-2017-0094161

(51) Int. Cl.
| | | |
|---|---|---|
| C07C 67/02 | (2006.01) | |
| B01J 27/02 | (2006.01) | |
| C07C 67/54 | (2006.01) | |
| C07C 67/03 | (2006.01) | |
| C07C 67/08 | (2006.01) | |
| C07C 69/68 | (2006.01) | |

(52) U.S. Cl.
CPC ............... *C07C 67/02* (2013.01); *B01J 27/02* (2013.01); *C07C 67/03* (2013.01); *C07C 67/08* (2013.01); *C07C 67/54* (2013.01); *C07C 69/68* (2013.01)

(58) Field of Classification Search
CPC .......... C07C 67/02; C07C 67/03; C07C 67/08
See application file for complete search history.

(56) References Cited

U.S. PATENT DOCUMENTS

| | | | | |
|---|---|---|---|---|
| 5,210,296 | A * | 5/1993 | Cockrem .............. | C07C 67/08 560/179 |
| 5,264,617 | A * | 11/1993 | Brake .................. | C08F 8/50 560/179 |
| 7,297,809 | B2 * | 11/2007 | Martino-Gauchi ..... | C07C 67/08 560/179 |
| 9,012,685 | B2 * | 4/2015 | Hwang ................ | C07C 51/493 562/589 |
| 9,249,073 | B2 * | 2/2016 | Van Krieken ......... | C07C 29/095 |

FOREIGN PATENT DOCUMENTS

| | | | | | |
|---|---|---|---|---|---|
| CN | 103922970 | | * | 7/2014 | .......... C07C 267/00 |
| KR | 10-2005-0085397 | A | | 8/2005 | |
| KR | 10-2011-0035303 | A | | 4/2011 | |
| KR | 10-2012-0060446 | A | | 6/2012 | |
| KR | 10-2015-0119141 | A | | 10/2015 | |

OTHER PUBLICATIONS

CN10392297, Na Li, Preparation of dicyclohexyl cabodiimide, English Abstract, 2 pages (Year: 2014).*

* cited by examiner

*Primary Examiner* — Yate' K Cutliff
(74) *Attorney, Agent, or Firm* — Seed IP Law Group LLP

(57) ABSTRACT

Provided is a method of efficiently preparing alkyl lactate from by-products which are generated during a process of converting lactic acid into lactide, or from poly(lactic acid) (PLA).

9 Claims, No Drawings

METHOD FOR PRODUCING ALKYL LACTATE

TECHNICAL FIELD

The present disclosure relates to a method of efficiently preparing alkyl lactate from by-products, which are generated during a process of converting lactic acid into lactide, or from poly(lactic acid) (PLA).

BACKGROUND ART

Alkyl lactate is a representative eco-friendly solvent with low volatility, excellent solubility, and nontoxic properties. In addition, alkyl lactate may be used as a food additive because it is biodegradable, and alkyl lactate may also be used as cleaners for solid surfaces contaminated with grease, adhesives, paints, or mechanical oils, or solvents for paints and coatings, because it may replace petroleum-based solvents.

On the other hand, due to recent environmental problems, biodegradable plastics have been actively studied. Among them, commercially valuable poly(lactic acid) (PLA) is the most actively studied, and is applied in various polymer products such as medical materials, packaging materials, etc. As a method of preparing poly(lactic acid), there are known a method of converting lactic acid into lactide, and sequentially, preparing poly(lactic acid) therefrom, in addition to a method of directly polymerizing lactic acid. At this time, during the preparation reaction of lactide, unreacted lactic acid, meso-lactide, water, and/or lactic acid oligomers are generated as by-products, which are generally separated and discarded during a process of purifying lactide.

In addition, biodegradable poly(lactic acid), of which production and consumption are steadily increasing, is usually disposed of in landfills, but requires more than a year to complete degradation and more than 90 days even exposed to microorganisms.

As described, there is a demand to develop a method of treating by-products generated during the preparation process of lactide or discarded poly(lactic acid), or a method of preparing value-added products therefrom.

DISCLOSURE

Technical Solution

An object of the present disclosure is to provide a method of preparing alkyl lactate, the method including the steps of: reacting by-products generated during a process of converting lactic acid into lactide, or poly(lactic acid) (PLA) with alcohol and an acidic catalyst to prepare alkyl lactate (a trans-esterification reaction step); neutralizing the prepared alkyl lactate to prepare a neutralized solution of pH 6 to pH 9 (a neutralization step); and recovering the alkyl lactate from the neutralized solution (a recovery step).

Advantageous Effects

A method of preparing alkyl lactate according to the present disclosure may prepare alkyl lactate from generally discarded by-products, which are generated during a process of converting lactic acid into lactide, or from a poly(lactic acid) waste by a simple process of a trans-esterification reaction without a separate process such as hydrolysis, etc. Further, in the method of preparing alkyl lactate, ammonia gas is used as a basic material, instead of sodium hydroxide or sodium carbonate generally used, during a neutralizing step of neutralizing an acidic catalyst. The use of ammonia gas blocks hydrolysis of alkyl lactate, which may be caused by water generated during the general neutralizing step, thereby minimizing by-product generation. Accordingly, alkyl lactate may be produced with high efficiency and high yield.

Best Mode

This will be described in detail as follows. Meanwhile, each description and embodiment disclosed in the present disclosure may also be applied to other descriptions and embodiments. That is, all combinations of various elements disclosed in this disclosure are within the scope of the present disclosure. In addition, the scope of the present disclosure is not to be limited by the specific description described below.

To achieve the above objects, an aspect of the present disclosure is to provide a method of preparing alkyl lactate, the method including the steps of: reacting by-products generated during a process of converting lactic acid into lactide, or poly(lactic acid) (PLA) with alcohol and an acidic catalyst to prepare alkyl lactate (a trans-esterification reaction step); neutralizing the prepared alkyl lactate to prepare a neutralized solution of pH 6 to pH 9 (a neutralization step); and recovering the alkyl lactate from the neutralized solution (a recovery step).

As used herein, the term "alkyl lactate" is a lactic acid alkyl ester, and may be a basic ester compound produced from lactic acid and alcohol, e.g., alkanol. Most of these compounds may be biodegradable. Alkyl lactate is a non-toxic eco-friendly material, and may be used as a food additive or as a solvent in a variety of fields, because of low volatility, excellent solubility, and biodegradability. For example, C1 to C4 alkyl lactate may be used as a food additive, a fragrance, a water-rinsable degreaser, or a solvent component for paints or coatings, and C12 to C15 alkyl lactate may be used as a softener in cosmetic compositions.

In the present disclosure, "by-products generated during a process of converting lactic acid into lactide" refer to a collection of materials generated during the process of producing lactide from lactic acid. Generally, when lactide is prepared using lactic acid, lactide is separated from products, and then remaining by-products are discarded. The products produced during the process of preparing lactide may concomitantly include unreacted lactic acid, meso-lactide, water, and lactic acid oligomers, in addition to the desired compound, lactide. A composition ratio of these compounds varies. For example, the by-products may include one or more selected from the group consisting of unreacted lactic acid, meso-lactide, and lactic acid oligomers. Further, the by-products may include L-lactide and/or D-lactide before being separated or even after being separated through a separation process. In other words, the by-products may include one or more selected from the group consisting of meso-lactide, L-lactide, D-lactide, lactic acid, and lactic acid oligomers. The lactic acid oligomers may include dimers, trimers, and multimers of lactic acid, or mixtures thereof. The amount of lactide included in the by-products may be 70% by weight to 95% by weight, based on the total weight of the by-products, and the lactide refers to all forms of lactides, irrespective of meso-, D-, and L-forms. Specifically, the lactide may be included in an amount of 80% by weight to 93% by weight, and more specifically, 88% by weight to 92% by weight, based on the total weight of the by-products, but is not limited thereto.

The lactic acid oligomers may be included in an amount of 0.5% by weight to 5% by weight, specifically 1% by weight to 5% by weight, and more specifically 1% by weight to 3% by weight, based on the total weight of the by-products, and the lactic acid may be included in an amount of 3% by weight to 8% by weight, specifically 4% by weight to 7% by weight, and more specifically 5% by weight to 6% by weight, based on the total weight of the by-products, but is not limited thereto.

The process of preparing lactide, which may generates the above by-products, may include methods of preparing lactide known in the art without limitation, and for example, may include all of a method of using a microorganism and a chemical synthetic method. Although the different preparation methods are used, compositions of the by-products generated therefrom are similar to each other.

For example, poly(lactic acid) which may be used in the method of preparing alkyl lactate of the present disclosure may be poly(lactic acid) as it is or a hydrolysate thereof, and a molecular weight thereof is not limited.

In the present disclosure, poly(lactic acid) is a biodegradable and bioactive thermoplastic aliphatic polyester, which is directly polymerized from lactic acid or prepared from its dehydration condensation compound, lactide. Poly(lactic acid) may be derived from renewable resources such as corn starch, and is one of the most used bioplastics. Since wastes thereof may include a variety of contaminants, they may be chemically recycled by decomposing into monomers and resynthesizing, rather than mechanically recycled. As described above, poly(lactic acid) may be prepared from lactide, and alkyl lactate produced by the preparation method according to the present disclosure may be synthesized from lactide which is a raw material of poly(lactic acid) by a method known in the art. The method of preparing alkyl lactate according to the present disclosure may be used for the purpose of recycling the discarded poly(lactic acid).

The method of preparing alkyl lactate according to the present disclosure includes the step (trans-esterification reaction step) of reacting the by-products generated during the process of converting lactic acid into lactide, or poly(lactic acid) with alcohol and an acidic catalyst to prepare alkyl lactate.

The trans-esterification reaction may be performed at 80° C. to 120° C. under atmospheric pressure, but is not limited thereto. The reaction temperature and pressure may be complementarily controlled. For example, the reaction temperature and pressure may be selected in combination, depending on the kinds of reactants and/or the catalyst.

Specifically, the trans-esterification reaction step may be performed using sulfuric acid, hydrochloric acid, or nitric acid as the acidic catalyst, and more specifically, may be performed using sulfuric acid, but is not limited thereto. The amount of the acidic catalyst used in the trans-esterification reaction step may be calculated in the number of moles. For example, the acidic catalyst may be included at a molar ratio of 0.01 to 0.06 (the number of moles of the acidic catalyst/the number of moles of the produced lactic acid), based on the number of moles of the produced lactic acid, when the by-products generated during the process of converting lactic acid into lactide, or poly(lactic acid) may be hydrolyzed into lactic acid, but is not limited thereto. Specifically, a ratio of the number of moles of the acidic catalyst with respect to the number of moles of the lactic acid may be about 0.01 mole to about 0.04 mole, and more specifically, about 0.02 mole to about 0.03 mole, but is not limited thereto.

Specifically, in the trans-esterification reaction step, the alcohol may be C1 to C4 alcohol, but is not limited thereto. For example, the alcohol may be methanol or ethanol, but is not limited thereto. The amount of the alcohol used in the trans-esterification reaction may be calculated in the number of moles. For example, the alcohol may be included at a molar ratio of 2 to 5 (the number of moles of the alcohol/the number of moles of the produced lactic acid), based on the number of moles of the produced lactic acid, when the by-products generated during the process of converting lactic acid into lactide, or poly(lactic acid) may be hydrolyzed into lactic acid, but is not limited thereto. Specifically, the number of moles of the alcohol with respect to the number of moles of the lactic acid may be 2 times to 3 times, and more specifically, 2.2 times to 3 times, but is not limited thereto. For example, when the number of moles of the alcohol is less than 2 times with respect to 1 mole of the lactic acid, the esterification reaction of lactic acid and the esterification reaction of lactic acid oligomers may compete each other to form alkyl lactate oligomers. On the contrary, when the number of moles of the alcohol is more than 5 times with respect to 1 mole of the lactic acid, a step of removing unreacted alcohol should be included in the process of purifying alkyl lactate which is produced by esterification reaction, resulting in process inefficiency. Further, even though the step of removing alcohol is further performed, alcohol is not completely removed but still remains in the products, thereby reducing the yield of alkyl acetate.

The method of preparing alkyl lactate according to the present disclosure includes the step (neutralization step) of neutralizing the prepared alkyl lactate to prepare a neutralized solution of pH 6 to pH 9. The neutralization step is a step of neutralizing the reaction solution which has undergone the trans-esterification reaction by adding the acidic catalyst, and this step may be performed using ammonia gas which is a basic material, but is not limited thereto.

For example, the acidic catalyst added for the trans-esterification reaction may rather cause a reverse reaction by facilitating hydrolysis of the product alkyl lactate. Therefore, in order to increase the stability and/or yield of the product, the method may include the step of neutralizing by treatment with the basic material, prior to purification of the product alkyl lactate. Generally, as a method of neutralizing the reaction solution, there is known a method of neutralizing using a basic solution such as sodium hydroxide or sodium carbonate (U.S. Pat. No. 5,264,617). However, this method may produce water during neutralization, as in the following Reaction Scheme, and water may cause hydrolysis of alkyl lactate which is the desired compound to be finally recovered.

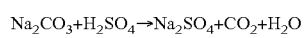
$$Na_2CO_3+H_2SO_4 \rightarrow Na_2SO_4+CO_2+H_2O$$

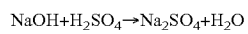
$$NaOH+H_2SO_4 \rightarrow Na_2SO_4+H_2O$$

For this reason, use of gaseous ammonia as the basic material for neutralization is advantageous in that generation of water causing a side reaction such as hydrolysis of alkyl lactate may be blocked, as in the following Reaction Scheme.

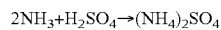
$$2NH_3+H_2SO_4 \rightarrow (NH_4)_2SO_4$$

Specifically, the neutralization step is to neutralize the reaction solution to pH 6 to pH 9 by treating, with the base, the reaction solution at lowered pH due to addition of the acidic catalyst.

The method of preparing alkyl lactate according to the present disclosure includes the step (recovery step) of recovering the final product alkyl lactate from the neutralized solution which is produced in the neutralization step. The recovery step may be performed by vacuum distillation of the neutralized solution, but is not limited thereto. The vacuum distillation as exemplified is the most widely used recovery method, but the method applicable in the recovery step of the present disclosure is not limited thereto. Various purification methods known in the art may be used without limitation, as long as the methods are able to recover alkyl lactate from the reaction liquid of a solution state containing alkyl lactate.

Specifically, the vacuum distillation for recovering alkyl lactate may be performed at a temperature of 30° C. to 90° C. and a pressure of 30 torr to 90 torr, but is not limited thereto. For example, the vacuum distillation may be performed at 30° C. to 50° C., or 50° C. to 80° C., but is not limited thereto. Further, the vacuum distillation may be performed at 30 torr to 50 torr, or 50 torr to 90 torr, but is not limited thereto. Specifically, an optimal combination of the temperature and the pressure for the vacuum distillation may be selected by considering them in the direction to maximize the reaction efficiency and/or the yield and recovery of the product, but is not limited thereto. For example, the vacuum distillation may be primarily performed under conditions of 30° C. to 40° C., and 50 torr to 90 torr to remove excess reactants, alcohol, and trace water, and then the vacuum distillation may be further performed under conditions of 50° C. to 80° C., and 30 torr to 50 torr to recover the desired compound, alkyl lactate, but is not limited thereto. Meanwhile, when distillation is performed at a high temperature of higher than 90° C., a polymerization reaction of unreacted lactic acid present in the neutralized solution occurs to generate a problem of producing lactic acid oligomers.

When the method of preparing alkyl lactate according to the present disclosure is used, alkyl lactate may be prepared at a conversion ratio of 90% or more from 'the by-products generated during the process of converting lactic acid into lactide' commonly discarded and/or from 'poly(lactic acid) waste' without a pretreatment process, and through the subsequent neutralization and recovery steps, alkyl lactate may be finally obtained with a high purity of 90% or more and a high yield.

MODE FOR INVENTION

Hereinafter, the present disclosure will be described in more detail with reference Examples. However, these Examples are for illustrative purposes only, and the scope of the present disclosure is not intended to be limited by these Examples.

REFERENCE EXAMPLE

A predetermined amount of by-products generated during a process of converting lactic acid into lactide, the by-products including meso-lactide, L/D-lactide, lactic acid oligomers, and lactic acid, or poly(lactic acid) (PLA) was taken, and dissolved in water, and then sodium hydroxide was added thereto to perform hydrolysis at 80° C. The hydrololysate was analyzed by high performance liquid chromatography (HPLC) to confirm that all components of the reactant were completely decomposed into lactic acid, and the number of mole of the produced lactic acid was calculated. The amounts of alcohol and an acidic catalyst used in the following Examples were determined by a molar ratio, based on the number of moles of the lactic acid produced when the by-products and the poly(lactic acid) were decomposed.

Example 1

50 g of by-products generated during a process of converting lactic acid into lactide, the by-products including 88% by weight of lactide (meso-lactide and L/D-lactide), 2% by weight of lactic acid oligomers, and 5% by weight of lactic acid, ethanol, and 98% sulfuric acid were introduced into a reactor, and then trans-esterification reaction was performed under stirring at 90° C. At this time, ethanol and 98% sulfuric acid were used in the number of moles of 2.2 times and 0.02 times with respect to the number of moles of lactic acid which was produced by degradation of all the components of the by-products, as calculated by the method of the Reference Example.

HPLC analysis was performed to examine whether conversion of ethyl lactate from the reaction solution occurred. The HPLC analysis was performed using HPLC (Agilent, USA) equipped with a diode array detector (DAD) of a wavelength of 230 nm and an RP-18 C18 column (Merck, USA). As a mobile solvent, a concentration gradient of a 0.2% aqueous phosphoric acid solution and acetonitrile containing 0.2% phosphoric acid was used, and a flow rate was set to 1 mL/min. Through this analysis, it was confirmed that the conversion to ethyl lactate was 89%.

The reaction mixture containing ethyl lactate which was produced by the reaction was cooled to room temperature, and then the pH was adjusted to 8 by bubbling ammonia gas into the reaction solution. Thereafter, vacuum distillation was performed at 30 torr to 50 torr and 50° C. to 80° C. to recover ethyl lactate. Karl-Fischer water analysis was performed to confirm that 1.23% of water was included, and liquid chromatography analysis was performed to confirm that the purity was 94%. The calculated final yield was 84%.

Example 2

50 g of by-products generated during a process of converting lactic acid into lactide, the by-products including 90% by weight of lactide (meso-lactide and L/D-lactide), 2% by weight of lactic acid oligomers, and 5% by weight of lactic acid, methanol, and 98% sulfuric acid were introduced into a reactor, and then trans-esterification reaction was performed under stirring at 90° C. At this time, methanol and 98% sulfuric acid were used in the number of moles of 2.2 times and 0.02 times with respect to the number of moles of lactic acid which was produced by degradation of all the components of the by-products, as calculated by the method of the Reference Example. After completion of the reaction, HPLC analysis was performed, and as a result, it was confirmed that conversion to methyl lactate was 89%.

The reaction mixture containing methyl lactate which was produced by the reaction was cooled to room temperature, and then the pH was adjusted to 8 by bubbling ammonia gas into the reaction solution. Thereafter, vacuum distillation was performed in the same manner as in Example 1 to remove remaining methanol and trace water, thereby obtaining methyl lactate with water of 1.68% and the purity of 93%. The final yield was 84%.

Example 3

70 g of poly(lactic acid) having a molecular weight of 100,000 g/mol (NatureWorks LLC, USA), ethanol, and 98% sulfuric acid were introduced into a reactor, and then trans-esterification reaction was performed under stirring at 90° C. At this time, ethanol and 98% sulfuric acid were used in the number of moles of 2.5 times and 0.02 times with respect to the number of moles of lactic acid which was produced by degradation of all the components of the poly(lactic acid), as calculated by the method of the Reference Example. After completion of the reaction, HPLC analysis was performed, and as a result, it was confirmed that conversion to ethyl lactate was 95%.

The reaction mixture containing ethyl lactate which was produced by the reaction was cooled to room temperature, and then the pH was adjusted to 7 by bubbling ammonia gas into the reaction solution. Thereafter, vacuum distillation was performed in the same manner as in Example 1 to remove remaining ethanol and trace water, thereby obtaining ethyl lactate with water of 2.16% and the purity of 95%. The final yield was 91%.

Example 4

700 g of by-products generated during a process of converting lactic acid into lactide, the by-products including 92% by weight of lactide (meso-lactide and L/D-lactide), 1% by weight of lactic acid oligomers, and 6% by weight of lactic acid, ethanol, and 98% sulfuric acid were introduced into a reactor, and then trans-esterification reaction was performed under stirring at 90° C. At this time, ethanol and 98% sulfuric acid were used in the number of moles of 2.5 times and 0.02 times with respect to the number of moles of lactic acid which was produced by degradation of all the components of the by-products, as calculated by the method of the Reference Example. After completion of the reaction, HPLC analysis was performed, and as a result, it was confirmed that conversion to ethyl lactate was 93%.

The reaction mixture containing ethyl lactate which was produced by the reaction was cooled to room temperature, and then the pH was adjusted to 8 by bubbling ammonia gas into the reaction solution. Thereafter, vacuum distillation was performed in the same manner as in Example 1 to remove remaining ethanol and trace water, thereby obtaining 1,076 g of ethyl lactate. At this time, the obtained ethyl lactate was confirmed to contain water of 1.84%. The purity analyzed by liquid chromatography was 94%, and the final yield was 90%.

Example 5

750 g of by-products generated during a process of converting lactic acid into lactide, the by-products including 90% by weight of lactide (meso-lactide and L/D-lactide), 2% by weight of lactic acid oligomers, and 5% by weight of lactic acid, ethanol, and 98% sulfuric acid were introduced into a reactor, and then trans-esterification reaction was performed under stirring at 90° C. At this time, ethanol and 98% sulfuric acid were used in the number of moles of 2.5 times and 0.02 times with respect to the number of moles of lactic acid which was produced by degradation of all the components of the by-products, as calculated by the method of the Reference Example. After completion of the reaction, HPLC analysis was performed, and as a result, it was confirmed that conversion to ethyl lactate was 92%.

The reaction mixture containing ethyl lactate which was produced by the reaction was cooled to room temperature, and then the pH was adjusted to 7 by bubbling ammonia gas into the reaction solution. Thereafter, vacuum distillation was performed in the same manner as in Example 1 to remove remaining ethanol and trace water, thereby obtaining 1,116 g of ethyl lactate. At this time, the obtained ethyl lactate was confirmed to contain water of 1.74%. The purity analyzed by liquid chromatography was 96%, and the final yield was 90%.

Comparative Example 1: Preparation of Alkyl Lactate by Neutralization Using a Basic Solution 1

750 g of by-products generated during a process of converting lactic acid into lactide, the by-products including 90% by weight of lactide (meso-lactide and L/D-lactide), 2% by weight of lactic acid oligomers, and 5% by weight of lactic acid, ethanol, and 98% sulfuric acid were introduced into a reactor, and then trans-esterification reaction was performed under stirring at 90° C. At this time, ethanol and 98% sulfuric acid were used in the number of moles of 2.2 times and 0.02 times with respect to the number of moles of lactic acid which was produced by degradation of all the components of the by-products, as calculated by the method of the Reference Example. After completion of the reaction, HPLC analysis was performed, and as a result, it was confirmed that conversion to ethyl lactate was 89%.

A 10 N aqueous sodium hydroxide solution in an amount equivalent to sulfuric acid used in the above reaction was added to the reaction mixture containing ethyl lactate which was produced by the reaction. Thereafter, vacuum distillation was performed in the same manner as in Example to remove remaining ethanol and trace water, thereby obtaining 780 g of ethyl lactate, together with 490 g of gel-type lactic acid oligomers which were produced by a polymerization reaction of lactic acid by hydrolysis of ethyl lactate. The product was analyzed by liquid chromatography, and as a result, the purity of the obtained ethyl lactate was 75%, and the final yield was 73%.

Comparative Example 2: Preparation of Alkyl Lactate by Neutralization Using a Basic Solution 2

50 g of by-products generated during a process of converting lactic acid into lactide, the by-products including 90% by weight of lactide (meso-lactide and L/D-lactide), 2% by weight of lactic acid oligomers, and 5% by weight of lactic acid, ethanol, and 98% sulfuric acid were introduced into a reactor, and then trans-esterification reaction was performed under stirring at 90° C. At this time, ethanol and 98% sulfuric acid were used in the number of moles of 2.5 times and 0.02 times with respect to the number of moles of lactic acid which was produced by degradation of all the components of the by-products, as calculated by the method of the Reference Example. After completion of the reaction, HPLC analysis was performed, and as a result, it was confirmed that conversion to ethyl lactate was 96%.

A 10 N aqueous sodium hydroxide solution in an amount equivalent to sulfuric acid used in the above reaction was added to the reaction mixture containing ethyl lactate which was produced by the reaction. Thereafter, vacuum distillation was performed in the same manner as in Example to remove remaining ethanol and trace water, thereby obtaining 62 g of ethyl lactate, together with gel-type lactic acid oligomers which were produced by a polymerization reaction of lactic acid by hydrolysis of ethyl lactate. The product was analyzed by liquid chromatography, and as a result, the purity of the obtained ethyl lactate was 76%, and the final yield was 76%.

RESULTS

First, to examine the effect according to the kind of alcohol in the method of preparing alkyl lactate according to the present disclosure, ethanol and methanol were used as the alcohol in Examples 1 and 2, respectively, and the by-products having the compositions similar to each other were used as the raw materials to prepare ethyl lactate and methyl lactate, respectively. The conversion ratio, purity, and yield were calculated and compared. As a result, all showed the similar values, indicating that high conversion ratio, and high purity and yield of the products were achieved, irrespective of the number of carbon atoms of alcohol used.

Further, to examine the effect according to the kind of the raw material in the method of preparing alkyl lactate according to the present disclosure, alkyl lactate was prepared by using poly(lactic acid) (Example 3), instead of the by-products generated during the process of converting lactic acid into lactide. As a result, the conversion ratio of 95%, the purity of 95%, and the final yield of 91% were obtained. All these values were equivalent to those of Examples 4 or 5 in which only the raw materials were different. In other words, even though non-pretreated poly(lactic acid) was used as the raw material, alkyl lactate could be prepared with high conversion ratio, and high purity and yield of the product.

Furthermore, to examine possibility of mass-production, in Examples 4 and 5, the reaction was performed under conditions in which the amount of the raw material was increased by 10 times or more, as compared to that of Example 1. As a result, even though the reaction was performed by increasing, in the same ratio, the amount of the by-products generated during the process of converting lactic acid into lactide as the raw material and the amounts of alcohol and sulfuric acid as the catalyst to be reacted with the by-products, alkyl lactate could be prepared with the equivalent or higher conversion ratio, purity, and yield of the product.

Meanwhile, in Examples 3 to 5, ethanol was used in the slightly increased amount, as compared with Example 1. As a result, when the number of moles of ethanol was increased from 2.2 times to 2.5 times with respect to the amount of lactic acid of the raw material, the conversion ratio into alkyl lactate by trans-esterification reaction showed about 4% increase.

Further, even though the compositions of the components of the by-products used in Examples 1, 2, 4 and 5 were different from each other, all Examples showed high levels of the conversion ratio, purity, and yield of the product. Therefore, in the method of preparing alkyl lactate of the present disclosure, by-products having various composition ratios may be used.

To examine the effect according to the difference in the neutralization step in the method of preparing alkyl lactate according to the present disclosure, Comparative Examples were prepared. In Comparative Examples, all procedures were performed in the same manner as in Examples, except for the neutralization step. In the neutralization step, the 10N aqueous sodium hydroxide solution corresponding to the equivalent weight of sulfuric acid was used, instead of ammonia gas. The conversion ratio, purity, and yield of alkyl lactate prepared by the methods of Comparative Examples were measured and compared with those of Examples, respectively. As a result, the conversion ratio was maintained at a high level of about 90% or more, whereas the purity of the purified alkyl lactate showed a reduction of about 20% or more, and the final yield also showed a reduction of 10% or more. Such a reduction of the purity and yield is attributed to formation of lactic acid oligomers as by-products. In other words, ethyl lactate is hydrolyzed into lactic acid by water generated during the neutralization step by sodium hydroxide, and the lactic acid is polymerized to produce gel-type lactic acid oligomers as by-products, thereby reducing the production yield and purity of ethyl lactate.

However, in the method of preparing alkyl lactate of the present disclosure, water production by the neutralization reaction may be minimized by using ammonia gas in the neutralization step, thereby blocking the side-reaction and remarkably improving the purity and yield of alkyl lactate.

The invention claimed is:

1. A method of preparing alkyl lactate, the method comprising the steps of:
reacting by-products generated during a process of converting lactic acid into lactide or poly(lactic acid) (PLA) directly with alcohol and an acidic catalyst to prepare alkyl lactate (a trans-esterification reaction step);
neutralizing the prepared alkyl lactate to prepare a neutralized solution of pH 6 to pH 9 (a neutralization step); and
recovering alkyl lactate from the neutralized solution (a recovery step),
wherein the neutralization step is performed by ammonia gas.

2. The method of preparing alkyl lactate of claim 1, wherein the by-products include one or more selected from the group consisting of meso-lactide, L-lactide, D-lactide, lactic acid, and lactic acid oligomers.

3. The method of preparing alkyl lactate of claim 1, wherein the acidic catalyst of the trans-esterification reaction step is sulfuric acid, hydrochloric acid, or nitric acid.

4. The method of preparing alkyl lactate of claim 1, wherein the number of moles of the acidic catalyst of the trans-esterification reaction step is included at a molar ratio of 0.01 to 0.06, based on the number of moles of the lactic acid produced by hydrolysis of the by-products or the poly(lactic acid).

5. The method of preparing alkyl lactate of claim 1, wherein the alcohol of the trans-esterification reaction step is C1 to C4 alcohol.

6. The method of preparing alkyl lactate of claim 1, wherein the alcohol of the trans-esterification reaction step is methanol or ethanol.

7. The method of preparing alkyl lactate of claim 1, wherein the number of moles of the alcohol of the trans-esterification reaction step is included at a molar ratio of 2 to 5, based on the number of moles of the lactic acid produced by hydrolysis of the by-products or the poly(lactic acid).

8. The method of preparing alkyl lactate of claim 1, wherein the recovery step is performed by vacuum distillation of the neutralized solution.

9. The method of preparing alkyl lactate of claim 8, wherein the vacuum distillation is performed at a temperature of 30° C. to 90° C. and a pressure of 30 torr to 90 torr.

* * * * *